(12) United States Patent
Grim et al.

(10) Patent No.: US 10,449,078 B2
(45) Date of Patent: Oct. 22, 2019

(54) MODULAR SYSTEM FOR AN ORTHOPEDIC WALKING BOOT

(71) Applicant: OVATION MEDICAL, Agoura Hills, CA (US)

(72) Inventors: Tracy E. Grim, Thousand Oaks, CA (US); Steven L. Hecker, Los Angeles, CA (US); Kenji Watabe, Ventura, CA (US); Ryan C. Cohn, Torrance, CA (US); Tim Crowley, Ventura, CA (US); Veneza Yuzon, Calabasas, CA (US)

(73) Assignee: Ovation Medical, Agoura Hills, CA (US)

(*) Notice: Subject to any disclaimer, the term of this patent is extended or adjusted under 35 U.S.C. 154(b) by 909 days.

(21) Appl. No.: 14/214,144

(22) Filed: Mar. 14, 2014

(65) Prior Publication Data

US 2014/0276301 A1    Sep. 18, 2014

Related U.S. Application Data

(60) Provisional application No. 61/801,930, filed on Mar. 15, 2013.

(51) Int. Cl.
*A61F 5/01* (2006.01)

(52) U.S. Cl.
CPC .................................. *A61F 5/0127* (2013.01)

(58) Field of Classification Search
CPC .................. A61F 5/0111; A61F 5/0585; A61F 2005/0172; A61F 5/0102; A61F 5/0104; A61F 5/0123; A61F 5/0195; A61F 5/012; A61F 5/0127; A61F 5/0113; A61F 13/043; A61F 13/045; A63C 13/003; A63C 13/005; A63C 13/006; A63C 2203/06; A63C 5/02; A63C 9/00; A63C 9/06; A63C 17/02; A63C 17/226; A63C 17/262;

(Continued)

(56) References Cited

U.S. PATENT DOCUMENTS 143,537 A    10/1873    Silberschmidt
1,472,415 A    10/1923    Haggerty (Continued)

FOREIGN PATENT DOCUMENTS

CN    201085714 Y    7/2008
CN    201523712 U    7/2010

(Continued)

OTHER PUBLICATIONS

PCT Publication No. WO/87/03471, dated Jun. 18, 1987, regarding PCT Application No. PCT/US86/02670.

(Continued)

*Primary Examiner* — Kari K Rodriquez
(74) *Attorney, Agent, or Firm* — Fulwider Patton LLP; Michael J. Moffatt, Esq.

(57) ABSTRACT

A base for an orthopedic walking boot having a foot bed configured to support a plantar portion of a user's foot, a section extending from the foot bed configured to surround a portion of user's foot, and a connector assembly matable with each of a plurality of different types of support structures such that any one of the plurality of different types of support structures is selectively and permanently connectable to the base through the at least one connector assembly.

2 Claims, 16 Drawing Sheets

(58) Field of Classification Search
CPC . A63C 17/0046; A63C 17/0073; A63C 17/16; A63C 17/20; A63C 17/223; A63C 2017/0053; A63C 9/086; A63C 9/0807; A63C 10/10; A63C 9/08528; A63C 10/103; A63C 10/18; A63C 10/106; A63C 10/145; A63C 10/24; A63C 9/08564; A63C 9/08578; A63C 9/006; A63C 9/08585; A63C 9/10; A63C 7/102; A63C 9/0844; A63C 9/0845; A63C 9/0847; A63C 9/001; A43B 7/141; A43B 7/28; A43B 23/28; A43B 7/20; A43B 5/047; A43B 5/0472; A43B 5/0474; A61H 2201/1697; A63B 2031/112; A63B 2031/115; A63B 31/12
USPC .............................. 602/12, 16, 23–28, 60–62
See application file for complete search history.

(56) References Cited

U.S. PATENT DOCUMENTS

| | | |
|---|---|---|
| 2,643,468 A | 6/1953 | Gottschalk |
| 2,959,169 A | 11/1960 | Bless |
| 3,464,126 A | 9/1969 | Sarkissian |
| 3,504,668 A | 4/1970 | Boudon |
| 3,661,151 A | 5/1972 | Schoenbrun et al. |
| 3,665,619 A | 5/1972 | Gray |
| 3,792,537 A | 2/1974 | Plank et al. |
| 3,805,773 A | 4/1974 | Sichau |
| 3,814,088 A | 6/1974 | Raymond |
| 3,955,565 A | 5/1976 | Johnson |
| 3,976,059 A | 8/1976 | Lonardo |
| 4,005,704 A | 2/1977 | Stöhr et al. |
| 4,053,995 A | 10/1977 | Shein |
| 4,057,056 A | 11/1977 | Payton |
| 4,094,312 A | 6/1978 | Whyte |
| 4,100,686 A | 7/1978 | Sgarlato et al. |
| 4,100,918 A | 7/1978 | Glancy |
| 4,184,273 A | 1/1980 | Boyer et al. |
| 4,188,735 A | 2/1980 | Hahn |
| 4,215,491 A | 8/1980 | Giannetti |
| 4,217,706 A | 8/1980 | Vartanian |
| 4,265,033 A | 5/1981 | Pois |
| 4,268,931 A | 5/1981 | Salomon |
| 4,393,866 A | 7/1983 | Finnieston |
| 4,446,856 A | 5/1984 | Jordan |
| 4,454,871 A | 6/1984 | Mann et al. |
| 4,494,536 A | 1/1985 | Latenser |
| 4,497,070 A | 2/1985 | Cho |
| 4,505,269 A | 3/1985 | Davies et al. |
| 4,510,927 A | 4/1985 | Peters |
| 4,550,721 A | 11/1985 | Michel |
| 4,556,054 A | 12/1985 | Paulseth |
| 4,559,934 A | 12/1985 | Philipp |
| 4,567,678 A | 2/1986 | Morgan et al. |
| 4,572,169 A | 2/1986 | Mauldin et al. |
| 4,587,962 A | 5/1986 | Greene et al. |
| 4,590,932 A | 5/1986 | Wilkerson |
| 4,624,247 A | 11/1986 | Ford |
| 4,628,945 A | 12/1986 | Johnson, Jr. |
| 4,665,904 A | 5/1987 | Lerman |
| 4,771,768 A | 9/1988 | Crispin |
| 4,805,601 A | 2/1989 | Eischen, Sr. |
| 4,825,856 A | 5/1989 | Nelson |
| 4,844,094 A | 7/1989 | Grim |
| 4,862,900 A | 9/1989 | Hefele |
| 4,872,273 A | 10/1989 | Smeed |
| 4,879,822 A | 11/1989 | Hayes |
| 4,919,118 A | 4/1990 | Morris |
| 4,941,271 A | 7/1990 | Lakic |
| 4,947,838 A | 8/1990 | Giannetti |
| 4,964,402 A | 10/1990 | Grim et al. |
| 4,974,583 A | 12/1990 | Freitas |
| 4,982,733 A | 1/1991 | Broadhurst et al. |
| 4,999,932 A | 3/1991 | Grim |
| 5,020,523 A | 6/1991 | Bodine |
| 5,078,128 A | 1/1992 | Grim et al. |
| 5,086,761 A | 2/1992 | Ingram |
| 5,088,478 A | 2/1992 | Grim |
| 5,088,479 A | 2/1992 | Detoro |
| 5,088,481 A | 2/1992 | Darby |
| 5,092,321 A | 3/1992 | Spademan |
| 5,125,400 A | 6/1992 | Johnson, Jr. |
| 5,154,695 A | 10/1992 | Farris et al. |
| 5,176,623 A | 1/1993 | Stetman et al. |
| 5,197,942 A | 3/1993 | Brady |
| 5,213,564 A | 5/1993 | Johnson, Jr. et al. |
| 5,219,324 A | 6/1993 | Hall |
| 5,226,245 A | 7/1993 | Lamont |
| 5,226,875 A | 7/1993 | Johnson |
| 5,233,767 A | 8/1993 | Kramer |
| 5,242,379 A | 9/1993 | Harris et al. |
| 5,277,695 A | 1/1994 | Johnson, Jr. et al. |
| RE34,661 E | 7/1994 | Grim |
| 5,329,705 A | 7/1994 | Grim et al. |
| 5,330,419 A | 7/1994 | Toronto |
| 5,334,135 A | 8/1994 | Grim et al. |
| 5,352,189 A | 10/1994 | Schumann et al. |
| 5,353,525 A | 10/1994 | Grim |
| 5,367,789 A | 11/1994 | Lamont |
| 5,368,551 A * | 11/1994 | Zuckerman ........... A61F 5/0111 602/23 |
| 5,370,133 A | 12/1994 | Darby et al. |
| 5,370,604 A | 12/1994 | Bernardoni |
| 5,378,223 A | 1/1995 | Grim et al. |
| 5,383,290 A | 1/1995 | Grim |
| 5,384,970 A | 1/1995 | Melton |
| 5,392,534 A | 2/1995 | Grim |
| 5,399,152 A | 3/1995 | Habermeyer et al. |
| 5,399,155 A | 3/1995 | Strassburg et al. |
| 5,407,421 A | 4/1995 | Goldsmith |
| 5,425,701 A | 6/1995 | Oster et al. |
| 5,426,872 A | 6/1995 | Hayes |
| 5,429,588 A | 7/1995 | Young et al. |
| 5,441,015 A | 8/1995 | Farley |
| 5,445,602 A | 8/1995 | Grim et al. |
| 5,460,599 A | 10/1995 | Davis et al. |
| 5,464,385 A | 11/1995 | Grim |
| 5,483,757 A | 1/1996 | Frykberg |
| 5,496,263 A | 3/1996 | Fuller, II et al. |
| 5,503,622 A | 4/1996 | Wehr |
| 5,507,720 A | 4/1996 | Lampropoulos |
| 5,526,586 A | 6/1996 | Foscaro |
| 5,527,269 A | 6/1996 | Reithofer |
| 5,551,950 A | 9/1996 | Oppen |
| 5,554,104 A | 9/1996 | Grim |
| 5,571,077 A | 11/1996 | Klearman et al. |
| 5,577,998 A | 11/1996 | Johnson, Jr. et al. |
| 5,582,579 A | 12/1996 | Chism et al. |
| 5,609,570 A | 3/1997 | Lamont |
| 5,617,650 A | 4/1997 | Grim |
| 5,620,411 A | 4/1997 | Schumann et al. |
| 5,632,723 A | 5/1997 | Grim |
| 5,641,322 A | 6/1997 | Silver et al. |
| 5,675,839 A | 10/1997 | Gordon et al. |
| 5,761,834 A | 6/1998 | Grim et al. |
| 5,762,622 A | 6/1998 | Lamont |
| 5,772,619 A | 6/1998 | Corbett |
| 5,776,090 A | 7/1998 | Bergmann et al. |
| 5,799,659 A | 9/1998 | Stano |
| 5,823,981 A | 10/1998 | Grim et al. |
| 5,827,210 A | 10/1998 | Antar et al. |
| 5,827,211 A | 10/1998 | Sellinger |
| 5,833,639 A | 11/1998 | Nune et al. |
| 5,836,902 A | 11/1998 | Gray |
| 5,853,381 A | 12/1998 | Stevenson et al. |
| 5,857,987 A | 1/1999 | Habermeyer |
| 5,865,166 A | 2/1999 | Fitzpatrick et al. |
| 5,868,690 A | 2/1999 | Eischen, Sr. |
| 5,887,591 A | 3/1999 | Powell et al. |
| 5,891,073 A | 4/1999 | Deirmendjian et al. |
| 5,897,515 A | 4/1999 | Willner et al. |
| 5,897,520 A | 4/1999 | Gerig |

(56) References Cited

U.S. PATENT DOCUMENTS

| | | |
|---|---|---|
| 5,902,259 A | 5/1999 | Wilkerson |
| 5,913,841 A | 6/1999 | Lamont |
| 5,925,010 A | 7/1999 | Caprio, Jr. |
| 5,951,504 A | 9/1999 | Iglesias et al. |
| 5,954,075 A | 9/1999 | Gilmour |
| 5,961,477 A | 10/1999 | Turtzo |
| 5,980,475 A | 11/1999 | Gibbons |
| 5,993,404 A | 11/1999 | McNiel |
| 6,019,741 A | 2/2000 | Prieskorn |
| 6,021,780 A | 2/2000 | Darby |
| 6,024,712 A | 2/2000 | Iglesia et al. |
| 6,027,468 A | 2/2000 | Pick |
| 6,044,578 A | 4/2000 | Kelz |
| 6,056,712 A | 5/2000 | Grim |
| 6,126,625 A | 10/2000 | Lundberg |
| 6,154,983 A | 12/2000 | Austin |
| 6,155,998 A | 12/2000 | Gilmour |
| 6,189,172 B1 | 2/2001 | Baek |
| 6,228,044 B1 | 5/2001 | Jensen et al. |
| 6,247,250 B1 | 6/2001 | Hauser |
| 6,267,742 B1 | 7/2001 | Krivosha et al. |
| 6,277,087 B1 | 8/2001 | Hess et al. |
| 6,282,816 B1 | 9/2001 | Rosendahl |
| 6,282,818 B1 | 9/2001 | Lu |
| 6,334,854 B1 | 1/2002 | Davis |
| 6,350,246 B1 | 2/2002 | DeToro |
| 6,361,514 B1 | 3/2002 | Brown et al. |
| 6,361,515 B1 | 3/2002 | Gilmour |
| 6,374,516 B1 | 4/2002 | Bonaventure et al. |
| 6,406,450 B1 | 6/2002 | Kowalczyk et al. |
| 6,409,695 B1 | 6/2002 | Connelly |
| 6,432,073 B2 | 8/2002 | Prior et al. |
| 6,491,654 B2 | 12/2002 | Lamont |
| D473,654 S | 4/2003 | Iglesias et al. |
| 6,558,339 B1 | 5/2003 | Graham |
| 6,572,571 B2 | 6/2003 | Lowe |
| 6,648,843 B1 | 11/2003 | Marciano et al. |
| 6,656,145 B1 | 12/2003 | Morton |
| 6,682,497 B2 | 1/2004 | Jensen et al. |
| 6,699,209 B2 | 3/2004 | Turtzo |
| 6,722,060 B2 | 4/2004 | Okajima |
| 6,755,798 B2 | 6/2004 | McCarthy et al. |
| 6,796,058 B2 | 9/2004 | Potchatko |
| D500,855 S | 1/2005 | Pick et al. |
| 6,866,043 B1 | 3/2005 | Davis |
| 6,923,780 B2 | 8/2005 | Price et al. |
| 6,945,946 B2 | 9/2005 | Rooney |
| 6,945,947 B2 | 9/2005 | Ingimundarson et al. |
| 6,955,654 B2 | 10/2005 | Gilmour |
| 6,976,972 B2 | 12/2005 | Bradshaw |
| 6,979,287 B2 | 12/2005 | Elbaz et al. |
| 6,991,613 B2 | 1/2006 | Sensabaugh |
| 7,018,351 B1 | 3/2006 | Iglesias et al. |
| 7,018,352 B2 | 3/2006 | Pressman et al. |
| D519,211 S | 4/2006 | Doty et al. |
| 7,077,818 B2 | 7/2006 | Ingimundarson et al. |
| 7,163,518 B1 | 1/2007 | Roche et al. |
| 7,163,519 B2 | 1/2007 | Price et al. |
| 7,182,743 B2 | 2/2007 | Slautterback et al. |
| D541,085 S | 4/2007 | Marsilio |
| 7,288,076 B2 | 10/2007 | Grim et al. |
| 7,294,114 B1 | 11/2007 | Clement et al. |
| 7,303,538 B2 | 12/2007 | Grim et al. |
| 7,311,686 B1 | 12/2007 | Iglesias et al. |
| 7,354,411 B2 | 4/2008 | Perry et al. |
| 7,384,584 B2 | 6/2008 | Jerome et al. |
| 7,475,501 B1 | 1/2009 | DeToro et al. |
| 7,563,238 B1 | 7/2009 | Breashears |
| 7,569,022 B2 | 8/2009 | Morinaka |
| 7,585,285 B2 | 9/2009 | Pone et al. |
| 7,597,674 B2 | 10/2009 | Hu et al. |
| 7,666,157 B2 | 2/2010 | Win |
| D616,556 S | 5/2010 | Hu |
| 7,727,173 B2 | 6/2010 | Rooney |
| 7,727,174 B2 | 6/2010 | Chang et al. |
| 7,743,532 B2 | 6/2010 | Bledsoe et al. |
| D619,726 S | 7/2010 | Win |
| 7,758,529 B2 | 7/2010 | Jensen et al. |
| 7,867,182 B2 | 1/2011 | Iglesias et al. |
| D634,438 S | 3/2011 | Hu |
| 7,896,826 B2 | 3/2011 | Hu et al. |
| 7,918,813 B2 | 4/2011 | Drake et al. |
| D640,792 S | 6/2011 | Anderson et al. |
| D641,084 S | 7/2011 | Anderson et al. |
| D642,695 S | 8/2011 | Anderson et al. |
| 8,002,724 B2 | 8/2011 | Hu et al. |
| D645,153 S | 9/2011 | Anderson et al. |
| 8,012,112 B2 | 9/2011 | Barberio |
| 8,021,317 B2* | 9/2011 | Arnold ............... A43B 7/00 128/882 |
| D662,598 S | 6/2012 | Anderson et al. |
| 8,226,585 B2 | 7/2012 | Pick et al. |
| 8,251,932 B2 | 8/2012 | Fout |
| 8,251,936 B2 | 8/2012 | Fout et al. |
| 2002/0062579 A1 | 5/2002 | Caeran |
| 2002/0128574 A1 | 9/2002 | Darby |
| 2003/0196352 A1 | 10/2003 | Bledsoe et al. |
| 2004/0015112 A1 | 1/2004 | Salutterback et al. |
| 2004/0019307 A1* | 1/2004 | Grim ............... A61F 5/0195 602/27 |
| 2004/0030275 A1 | 2/2004 | Morinaka |
| 2005/0172517 A1 | 8/2005 | Bledsoe et al. |
| 2005/0228332 A1 | 10/2005 | Bushby |
| 2005/0240133 A1 | 10/2005 | Rooney |
| 2005/0274046 A1 | 12/2005 | Schwartz |
| 2006/0032093 A1 | 2/2006 | Vannini |
| 2006/0048344 A1 | 3/2006 | Cavanagh et al. |
| 2006/0084899 A1 | 4/2006 | Verkade et al. |
| 2006/0189907 A1 | 8/2006 | Pick et al. |
| 2006/0217649 A1 | 9/2006 | Rabe |
| 2007/0010770 A1 | 1/2007 | Gildersleeve |
| 2007/0191749 A1 | 8/2007 | Barberio |
| 2007/0260164 A1 | 11/2007 | Chiodo et al. |
| 2007/0276307 A1 | 11/2007 | Erenstone |
| 2008/0004558 A1 | 1/2008 | Outred et al. |
| 2008/0098626 A1 | 5/2008 | Wright |
| 2008/0154166 A1 | 6/2008 | Beckwith et al. |
| 2008/0269656 A1* | 10/2008 | Arnold ............... A43B 7/00 602/28 |
| 2008/0294082 A1 | 11/2008 | Chang et al. |
| 2008/0294083 A1 | 11/2008 | Chang et al. |
| 2008/0302371 A1 | 12/2008 | Cohen et al. |
| 2008/0319362 A1 | 12/2008 | Joseph |
| 2009/0043234 A1 | 2/2009 | Bledsoe et al. |
| 2009/0076425 A1 | 3/2009 | Schwartz |
| 2009/0192427 A1 | 7/2009 | Brown et al. |
| 2009/0192428 A1 | 7/2009 | DeBoer et al. |
| 2009/0227927 A1 | 9/2009 | Frazer |
| 2009/0227928 A1 | 9/2009 | Drake et al. |
| 2009/0264803 A1 | 10/2009 | Darby, II et al. |
| 2009/0299246 A1 | 12/2009 | Pone et al. |
| 2009/0306565 A1 | 12/2009 | Chan |
| 2010/0069807 A1 | 3/2010 | Cox |
| 2010/0100018 A1* | 4/2010 | Fout ............... A61F 5/0111 602/13 |
| 2010/0106065 A1* | 4/2010 | Ward ............... A61F 5/0102 602/23 |
| 2010/0204631 A1 | 8/2010 | Rooney |
| 2010/0234782 A1 | 9/2010 | Hu et al. |
| 2010/0324461 A1 | 12/2010 | Darby |
| 2011/0009791 A1* | 1/2011 | Hopmann ............... A61F 5/0127 602/23 |
| 2011/0015555 A1* | 1/2011 | Anderson ............... A61F 5/0111 602/2 |
| 2011/0021963 A1 | 1/2011 | Graddon et al. |
| 2011/0066095 A1 | 3/2011 | Price et al. |
| 2011/0146032 A1 | 6/2011 | Hu et al. |
| 2011/0196275 A1 | 8/2011 | Chang et al. |
| 2011/0313336 A1 | 12/2011 | Chan |
| 2012/0000092 A1 | 1/2012 | Ingvarsson et al. |
| 2012/0010534 A1 | 1/2012 | Kubiak et al. |
| 2012/0010535 A1 | 1/2012 | Kubiak et al. |
| 2012/0035520 A1 | 2/2012 | Ingimundarson et al. |
| 2012/0065564 A1 | 3/2012 | Hoffmeier |

(56) References Cited

U.S. PATENT DOCUMENTS

| | | |
|---|---|---|
| 2012/0078148 A1 | 3/2012 | Hu et al. |
| 2012/0116275 A1 | 5/2012 | Pochatko |
| 2013/0066247 A1 | 3/2013 | Bird et al. |

FOREIGN PATENT DOCUMENTS

| | | |
|---|---|---|
| DE | 2341658 | 3/1974 |
| DE | 3228753 | 2/1984 |
| DE | 3909922 | 2/1990 |
| EP | 0095396 | 11/1983 |
| EP | 1006960 | 1/2003 |
| FR | 2399811 | 3/1979 |
| RU | 2165229 | 4/2001 |

OTHER PUBLICATIONS

Article from http://www.alimed.com regarding AliMed D2 Night Splint for Plantar Fasciitis.
Aircast Incorporated Product Brochure, "SP-Walker, short pneumatic walking brace", Jan. 11, 2002.
PCT Publication No. WO/2012/020251, dated Feb. 16, 2012, regarding PCT Application No. PCT/GB2011/051499.
PCT Publication No. WO/2005/097014, dated Oct. 20, 2005, regarding PCT Application No. PCT/SE2005/000513.
PCT Publication No. WO/2012/099989, dated Jul. 26, 2013, regarding PCT Application No. PCT/US2012/021763.
PCT Publication No. WO/2012/001678, dated Jan. 5, 2012, regarding PCT Application No. PCT/IL2011/000487.
Paul A. Dale, M.D. et al.; "A New Concept in Fracture Immobilization", Clinical Orthopaedics. Oct. 1993, vol. 295: 264-269.

\* cited by examiner

MODULAR SYSTEM FOR AN ORTHOPEDIC WALKING BOOT

CROSS REFERENCE TO RELATED APPLICATION

This application claim the benefit of U.S. Provisional Patent Application Ser. Nos. 61/801,930, filed Mar. 15, 2013, which is incorporated herein by reference.

BACKGROUND OF THE INVENTION

Field

The present disclosure relates generally to orthopedic walking boots.

Background

It is common that people, especially active and/or frail people, experience a variety of lower leg and ankle injuries. To aid in the treatment of the injuries it is desirable to immobilize the injury, typically above and below the affected joint.

Physicians traditionally will place patients in a cast that will start at the toes and end below the knee in what is called a short leg cast. Physicians have noticed that casts are hot, promote skin itching and will rub the leg when the swelling subsides.

An alternative to the short leg cast is a short leg walker, or a premanufactured walker, that is made of a rigid plastic frame lined with a soft padding to accommodate the leg comfortably. Many times the liner, or soft good, may house a series of air bladders that can be adjusted by the patient to improve the fit and help compress the swelling resulting in less pain and more stability. The walkers can be removed when directed to address skin issues, remove sutures or conduct passive range of motion exercises. Circumferential casts do not offer the luxury of easy on/off.

Walkers are essentially rigid encasing envelopes for the leg that usually immobilize the foot and ankle at a neutral position (or 90 degrees). The patient can walk easiest if the ankle is frozen at 90 degrees, otherwise the patient would be walking on the toes or on the heel. The sole is usually curved from front to back in a rocker bottom fashion to initiate a smoother stride from front to back allowing heel strike, rocking forward then toe-off for a successful step.

SUMMARY

Aspects of a base for an orthopedic walking boot include a foot bed configured to support a plantar portion of a user's foot, a section extending from the foot bed configured to surround a portion of user's foot, and a connector assembly matable with each of a plurality of different types of support structures such that any one of the plurality of different types of support structures is selectively and permanently connectable to the base through the at least one connector assembly Aspects of a base for an orthopedic walking boot also include a foot bed configured to support a plantar portion of the user's foot, a section extending from the foot bed configured to surround a portion of the user's foot, and a connector assembly matable with each of a strut structure and a clamshell structure such that any one of the strut structure or the clamshell structure is selectively and permanently connectable to the base through the at least one connector assembly Aspects of an orthopedic walking boot include a foot bed configured to support a plantar portion of a user's foot, a section extending from the foot bed configured to surround a portion of user's foot, and a connector assembly matable with each of a plurality of different types of support structures such that any one of the plurality of different types of support structures is selectively and permanently connectable to the base through the at least one connector assembly, and a support structure permanently connected to the base through the connector assembly.

DETAILED DESCRIPTION

Figure 1:
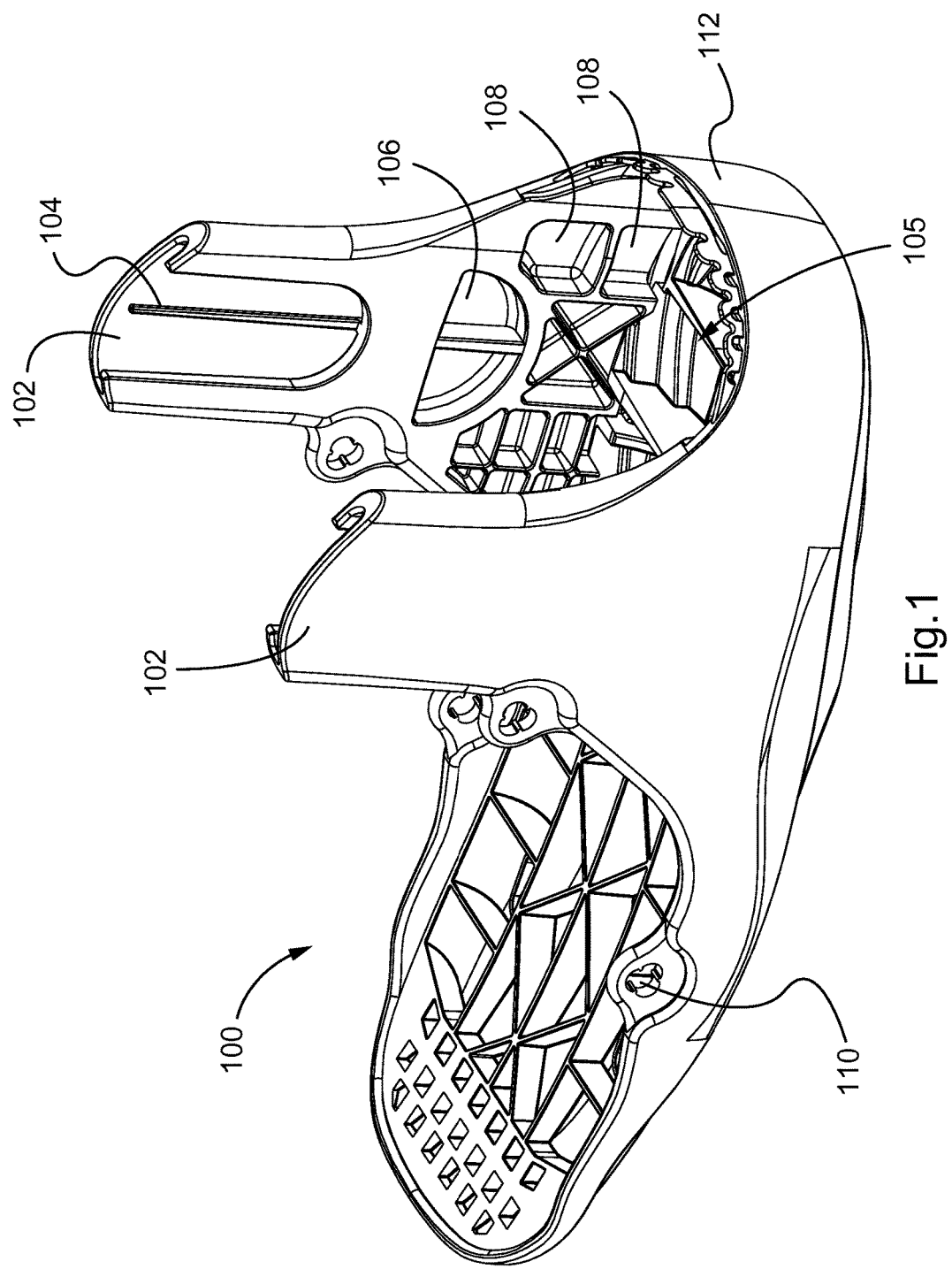
FIG. 1 is a perspective view of a base in accordance with aspects of the present invention.

Various aspects of the present invention will be described herein with reference to drawings that are schematic illustrations of idealized configurations of the present invention. As such, variations from the shapes of the illustrations as a result, for example, manufacturing techniques and/or tolerances, are to be expected. Thus, the various aspects of the present invention presented throughout this disclosure should not be construed as limited to the particular shapes of elements (e.g., regions, layers, sections, substrates, etc.) illustrated and described herein but are to include deviations in shapes that result, for example, from manufacturing. Thus, the elements illustrated in the drawings are schematic in nature and their shapes are not intended to illustrate the precise shape of an element and are not intended to limit the scope of the present invention, unless intentionally described as such.

It will be understood that when an element such as a region, layer, section, substrate, or the like, is referred to as being "on" another element, it can be directly on the other element or intervening elements may also be present. In contrast, when an element is referred to as being "directly on" another element, there are no intervening elements present. It will be further understood that when an element such as a structure is referred to as being coupled to another element, it can be directly connected to the other element or intervening elements may also be present. Similarly, two elements may be mechanically coupled by being either directly physically connected, or intervening connecting elements may be present. It will be further understood that when an element is referred to as being "formed" on another element, it can be deposited, attached, connected, coupled, or otherwise prepared or fabricated on the other element or an intervening element.

Furthermore, relative terms, such as "lower" or "bottom" and "upper" or "top," may be used herein to describe one element's relationship to another element as illustrated in the drawings. It will be understood that relative terms are intended to encompass different orientations of an apparatus in addition to the orientation depicted in the drawings. By way of example, if a walker in the drawings is turned over, elements described as being on the "lower" side of other elements would then be oriented on the "upper" side of the other elements. The term "lower", can therefore, encompass both an orientation of "lower" and "upper," depending of the particular orientation of the walker. Similarly, if a walker in the drawing is turned over, elements described as "below" or "beneath" other elements would then be oriented "above" the other elements. The terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and this disclosure.

It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. The term "and/or" includes any and all combinations of one or more of the associated listed items.

The detailed description set forth below in connection with the appended drawings is intended as a description of various aspects of the present invention and is not intended to represent all aspects in which the present invention may be practiced. The detailed description includes specific details for the purpose of providing a thorough understanding of the present invention. However, it will be apparent to those skilled in the art that the present invention may be practiced without these specific details. In some instances, well-known structures and components are shown in block diagram form in order to avoid obscuring the concepts of the present invention.

Various aspects of the present invention may provide an improved short leg walker that may be fitted easily around the leg to provide support and allow ambulation for the affected limb.

Reference to various ranges may be used to describe certain aspects of the present invention. By way of example, a range may be used to describe variations of the bonding force at different points on an outer sole to describe an evenly distributed bonding of the outer sole to the base of the walker. By way of an example, an outer sole which provides evenly distributed bonding to the base of the walker may exhibit a narrower tolerance band of force values at all x,y coordinates on the bonding surface than tolerance band of any other attachment method of the outer sole to the base of the walker.

People often experience injuries to the lower leg and ankle. For example, blunt trauma, sports injuries and common falls are the primary causes. Injuries such as fractures of the bones or soft tissue injuries (e.g., ligamentous tears) have similar symptoms. Swelling, pain and inability to ambulate without support are expected and predictable. Some injuries need to be immobilized for a period of time for the injury to heal. The time required for ligamentous injuries to heal is similar to the time required for fractures to heal. A period of 4 to 6 weeks of immobilization is common. Different injuries require different rehab times and regimes.

Aspects of the present invention are directed to orthopedic walking boots. In an aspect of the prevention invention, an orthopedic walking boot may include bilateral struts which connect a base of the orthopedic walking boot to an upper portion of the orthopedic walking boot. The struts may be rigid and provided on either side of the leg. The bilateral struts may be held onto the limb with strapping systems that encircle at least a portion of the limb. In another aspect, the base may be attached a posterior piece which extends from the foot to the back of the leg and calf forming a clamshell configuration. In the clamshell configuration, a single piece encompasses the side of the leg (similar to the bilateral configuration) as well as the rear of the leg. The orthopedic walking boot may include an adjoining anterior piece that joins or overlaps the posterior piece and is held on by a traditional strapping system or with mechanical attachment mechanism. In another aspect, the orthopedic walking boot may comprise a "hybrid" configuration (also referred herein as a "multi-sectioned" configuration). In the hybrid configuration, the base may be attached to the bilateral struts of the bilateral configuration and also attached a separate/non-integral posterior element that encompasses the rear of leg (similar to the rear portion of the clamshell). In this manner, the bilateral struts surround the side of the legs while the separate posterior portion encompasses the rear of the leg. Thus, the hybrid configuration achieves a similar result as the clamshell with multiple sections, hence, "multi-sectioned." Thus, the leg support structures may be generally categorized into two different types. One type is a support structure surrounds and supports the outer side portion of the user's legs. For example, the first type may be a one or both struts of the bilateral strut configuration. A second type is a support structure that also surrounds and supports the outer side portion of the user's leg, but also extends behind the user's leg to provide additional protection and support. For example the second type may be the clamshell structure.

In an aspect, the orthopedic walking boot may be configured such that the portion that receives the user's foot (e.g., the base portion) extends at 90° degrees or at substantially 90° relative to a longitudinal axis of the portion that receives the user's leg (e.g., the upper portion). In another aspect, the orthopedic walking boot may include two struts rising from the base. The orthopedic walking boot may further include a soft component within the constraints of the struts and on top of the base. The soft component may be held by straps.

While plaster casts fit each patient relatively well as a colonnade for specific anatomy and may be considered as a custom piece, rigid walkers allow patients more flexibility and mobility as they heal, resulting in faster overall patient healing.

While many in the orthopedic walker industry have strived to provide a one size fits all product to serve the many custom needs of their patients, in many cases this proves to be an expensive business decision resulting in excessive and often unused inventory. In comparison, it is desirable to minimize the amount of parts, while providing the most number of discrete products as possible.

As discussed in more detail below, aspects of the present invention are directed to a modular orthopedic walking boot. A base part may serve as the foundation for several product lines, allowing substantially different walking boots be assembled from the same base.

Figure 6:
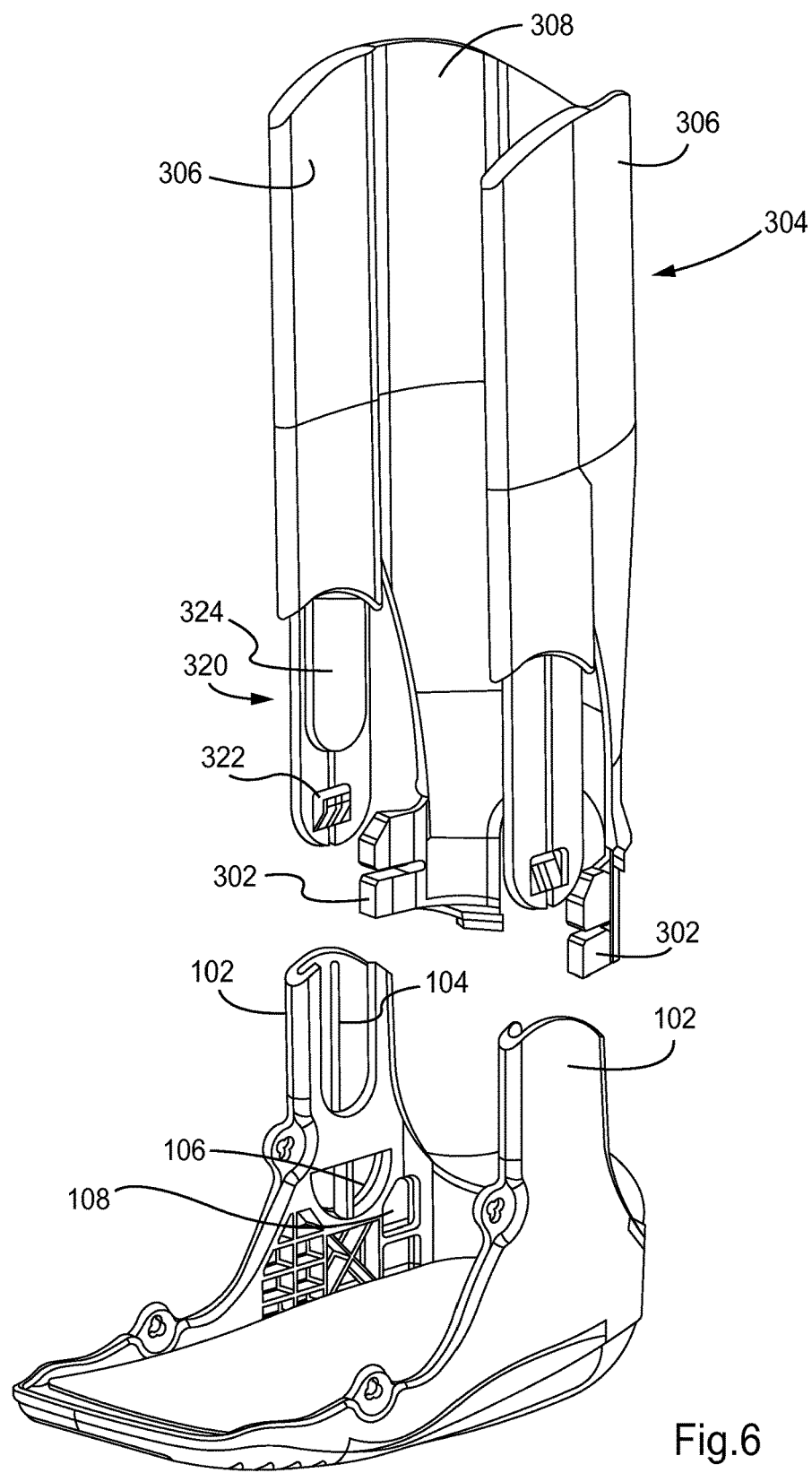
FIG. 6 is an exploded view of the base of FIG. 1 with a clamshell structure in accordance with aspects of the present invention.
Figure 7:
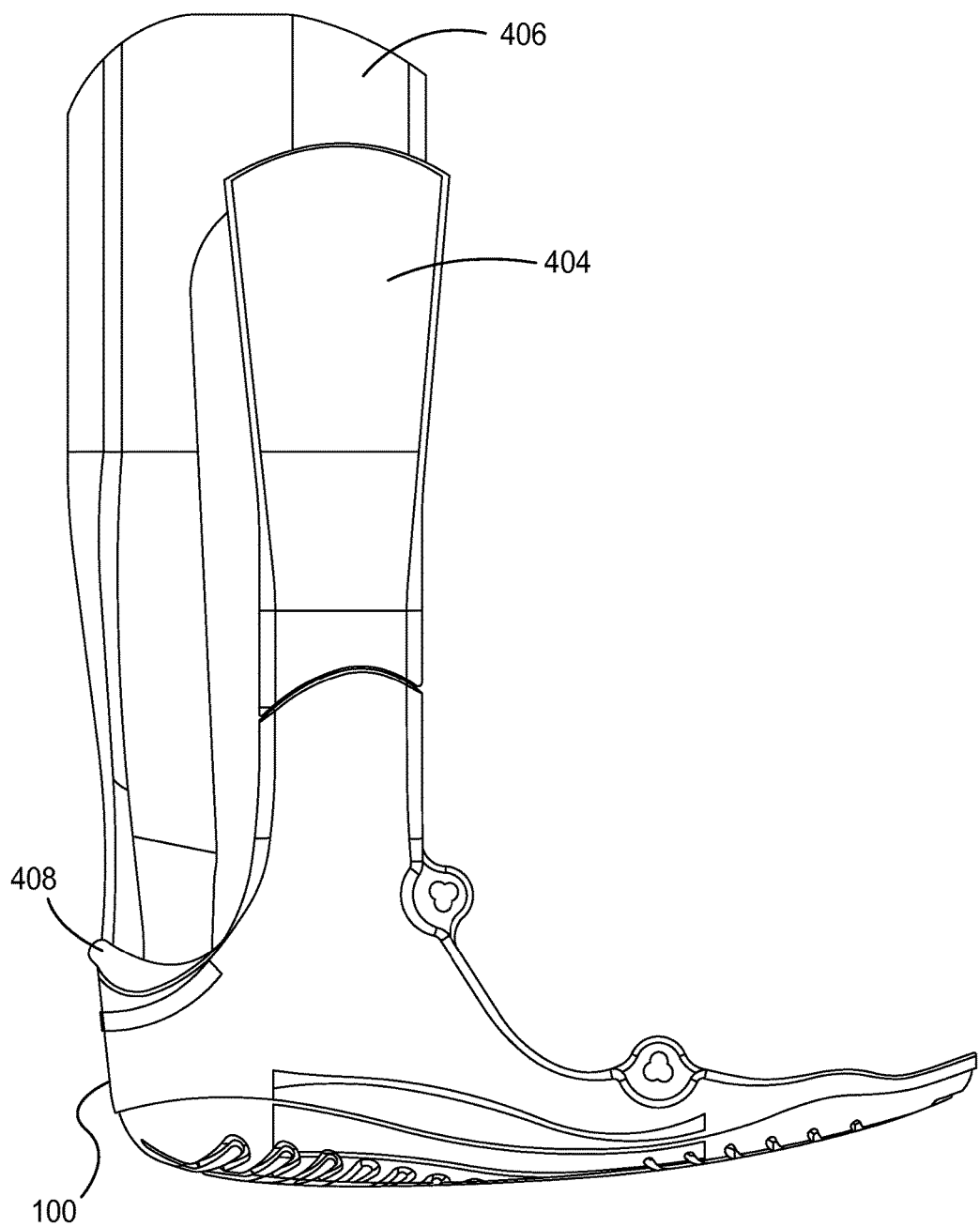
FIG. 7 is a side view of the base of FIG. 1 engaged with a non-continuous clamshell structure.
Figure 8:
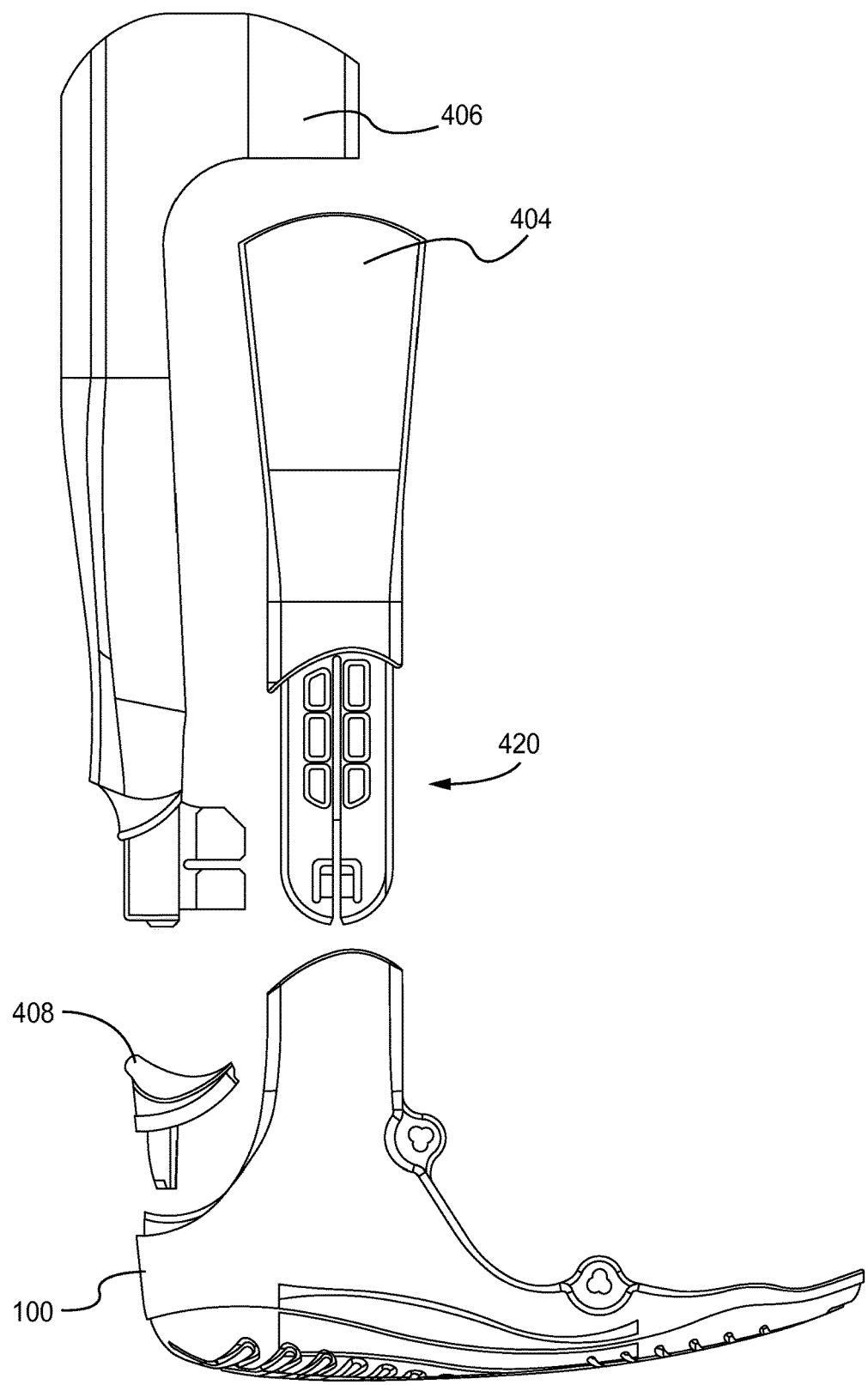
FIG. 8 is an exploded view of the base of FIG. 1 with a non-continuous clamshell structure.

FIG. 1 is a perspective view of a walker base 100 of a modular orthopedic walking boot. As is discussed below in more detail, the base 100 serves as the core part to which other discrete mating parts may be attached. The base 100 may include receiving features 102 configured to receive a variety of support structure (alternatively referred herein as "mating parts"). Example support structure, each of which are discussed in more detail below, include bilateral struts that form a bilateral orthopedic walking boot when mated with base (FIGS. 3 and 4), a posterior shell that extends behind the leg thus forming a clamshell when mated with the base (FIGS. 5 and 6), or a "hybrid" arrangement where two lateral struts similar to the bi-lateral type and a non-integral posterior piece are mated with the base (FIGS. 7 and 8). The base 100 may include a spine 104 that guides the mating parts into the base and strengthens the combined assembly of the base and mating part. The receiving features 102 may include snap engagement receiving portions 106 distributed proximate to footbed portion 105 of the base, to facilitate one-way fastening of the mating part with the receiving feature 102. As shown in the various figures, a section extending from the foot bed may be configured to surround a portion of user's foot. Other fastening means may be implemented including adhesives, mechanical fasteners, welding, overmolding and the like.

Additional snap engagement receiving elements 108 may be located at an area between the receiving feature 102 and a heel portion 112 of the base. The additional snap engagement receiving elements 108 may be used to secure a posterior element which will be discussed in greater detail below. The snap engagement receiving portions 108 may also be located on the side of the base opposing the engagement surfaces 108 viewable in FIG. 1. In other words, the base may be symmetrical about a longitudinal axis extending from the heel to the toe such that the side not viewable in FIG. 1 also includes snap engagement receiving elements. The snap engagement features may be interchangeable and may be selected based on the particular product.

The base may further include bosses 110 that may allow assembly of the base with various parts. For example, the bosses 100 may provide an anchoring point for strap anchor, which is discussed in more detail below with respect to FIGS. 9-11.

Figure 2:
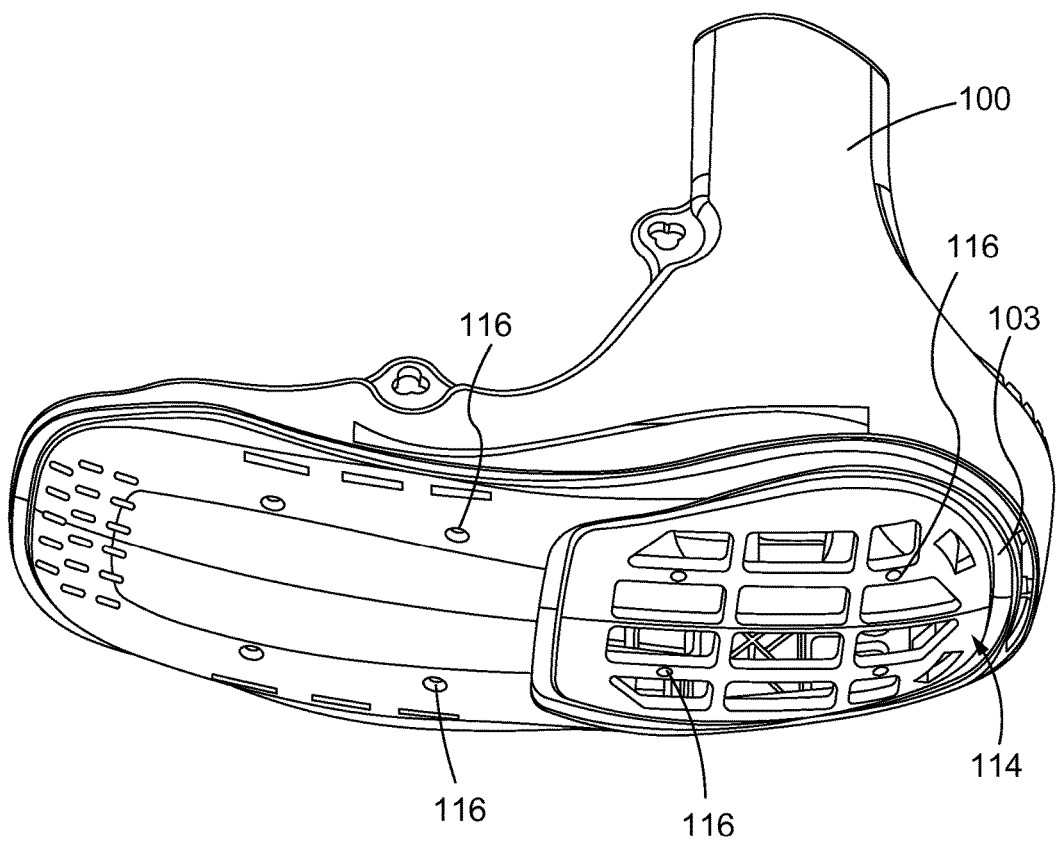
FIG. 2 is a bottom perspective view of the base of FIG. 1.

FIG. 2 is a bottom perspective view of the base 100. The base 100 may include a shock area 114. The shock area 114 may include engagement features 103 that may accept a number of different shock absorbing elements (not shown) having engaging features that mate with the engagement features of the shock area. A plurality of through holes 116 may aid in the attachment of an outer sole (not shown) to the plantar surface of the walker base 100. The shock absorbing element may be held in place to the shock area 114 by overmolding the outer sole over the shock absorbing element, or by any number of securing methods. The base may include a "dummy" part or spacer instead of a shock absorbing element to provide an orthopedic walking boot for those user's that do not desire the additional shock absorbing.

Figure 3:
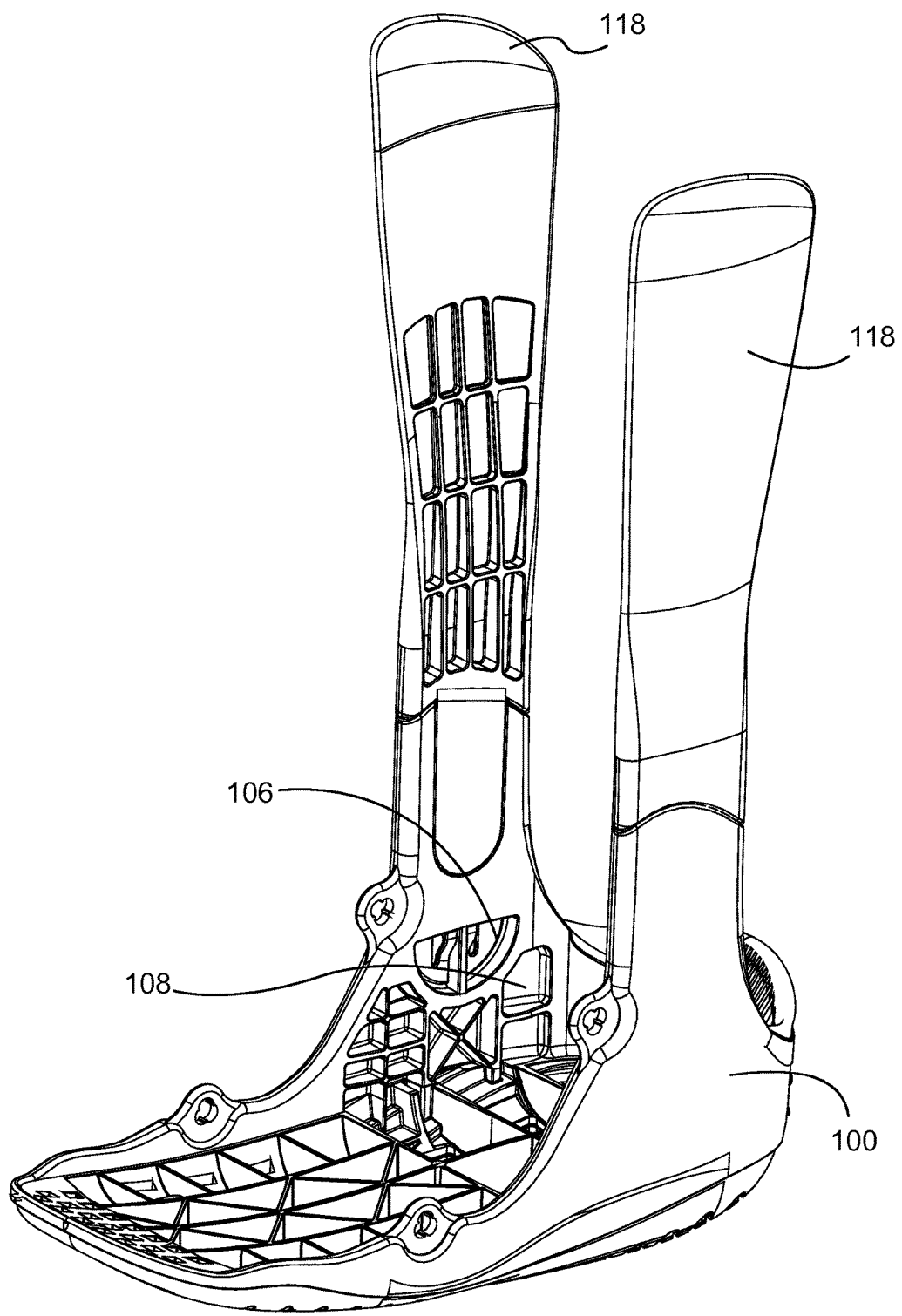
FIG. 3 is a perspective view the base of FIG. 1 engaged with struts in accordance with aspects of the present invention.

FIG. 3 is a perspective view of the base 100 with attached bilateral struts 118.

Figure 4:
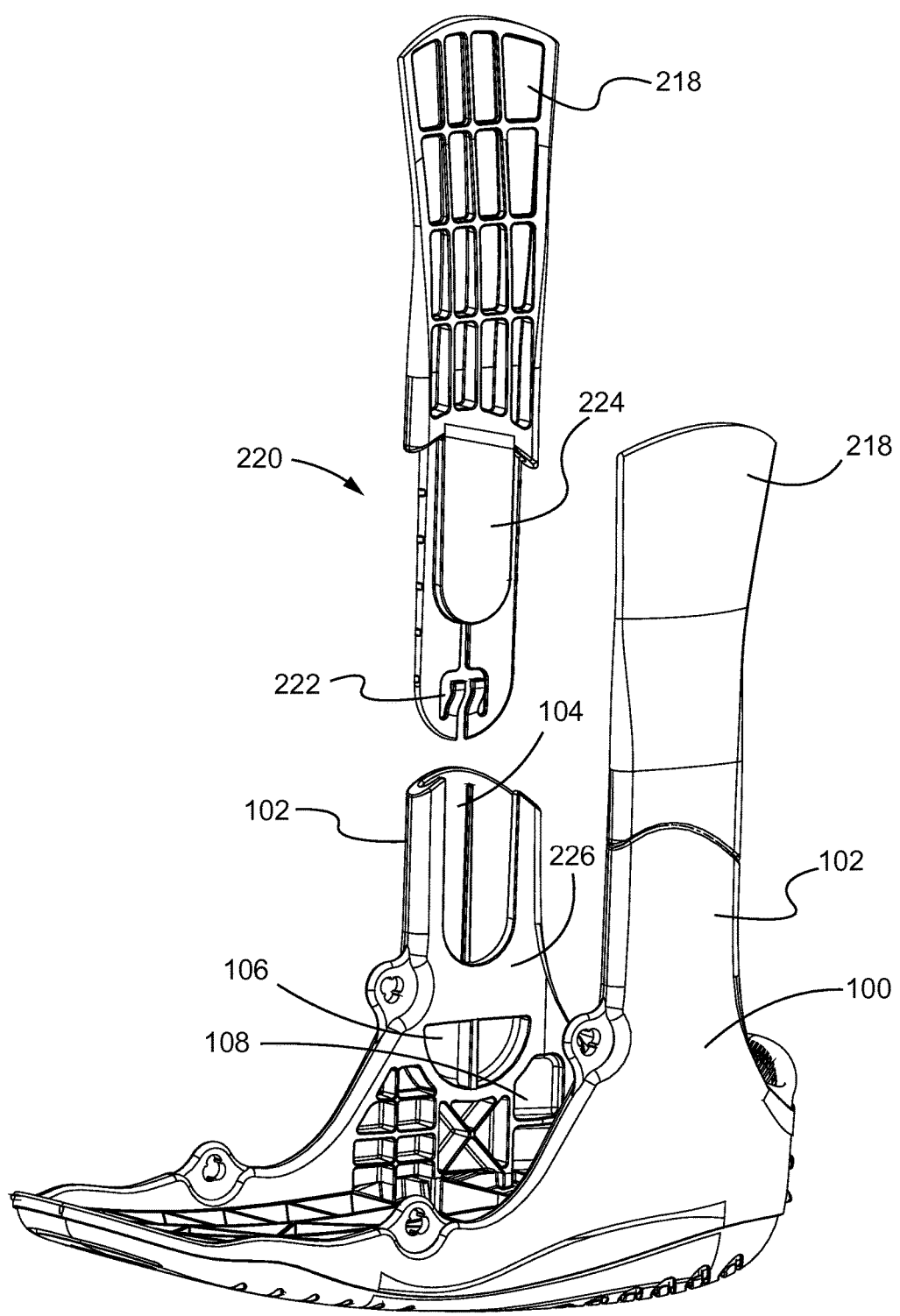
FIG. 4 is a partially exploded perspective view of the base of FIG. 1 with struts in accordance with aspects of the present invention.

The plurality of struts 118 may engage with the snap engagement surfaces 106 located on the base 100, the details of which are discussed with respect to FIG. 4. FIG. 4 shows a partially exploded view of the base 100 with attached struts 218. As shown in FIG. 4, while the same base 100 is used, the struts 218 attached to the base are shorter than the struts 118 shown in FIG. 3. However, the engagements of the struts 118, 218 to the base 100 are the same. As shown FIG. 4, the struts 218 may include a male engagement portion 220. The male engagement portion 220 may include a biasing member 222 and an alignment rib 224. The biasing member 222 may comprise a ramp that biases in a direction away from the strut 218 (i.e., toward the opposing strut). As shown in FIG. 4, prior to mating with the base, the biasing member 222 is fully extended.

To assemble the walking boot, the operator (e.g., a doctor) may insert the desired strut into (short, long, etc.) into the receiving feature 102 by aligning the strut with the spine 104. As the strut 118, 218 is slid into the receiving feature the alignment rib is aligned with the spine 104 and the biasing member 222 approaches the engagement receiving portion 106. In the fully extended state, the biasing member 222 projects beyond the thickness of the area between the spine 104 and the opposing wall 226. As the strut 118, 218 is further pushed into the receiving feature 102, the biasing member 222 will come into contact with the inner surface of the wall 226. As the biasing member is pushed further into the area between the spine 102 and the wall 226, the biasing member 222 will be compressed against the surface of the strut 118, 218. Once the biasing member 222 fully passes out of the area between the spine 104 and the wall 222, the biasing member enters the engagement receiving portion 106. As shown in FIG. 4, because the wall portion 226 is not longer present in the receiving engagement portion 106, the biasing member is free to return to the default state of extending fully toward the opposing strut. Once the biasing member 222 is extended, the strut 118, 218 can no longer be removed from the receiving feature 102 because the reverse motion (i.e., pulling on the strut 118, 218 in a direction away from the base 100) would cause the biasing member to press against the wall 226 without compressing the biasing member 222. In an example embodiment, the biasing member 222 may have a ramp shape to provide this functionality.

Figure 5:
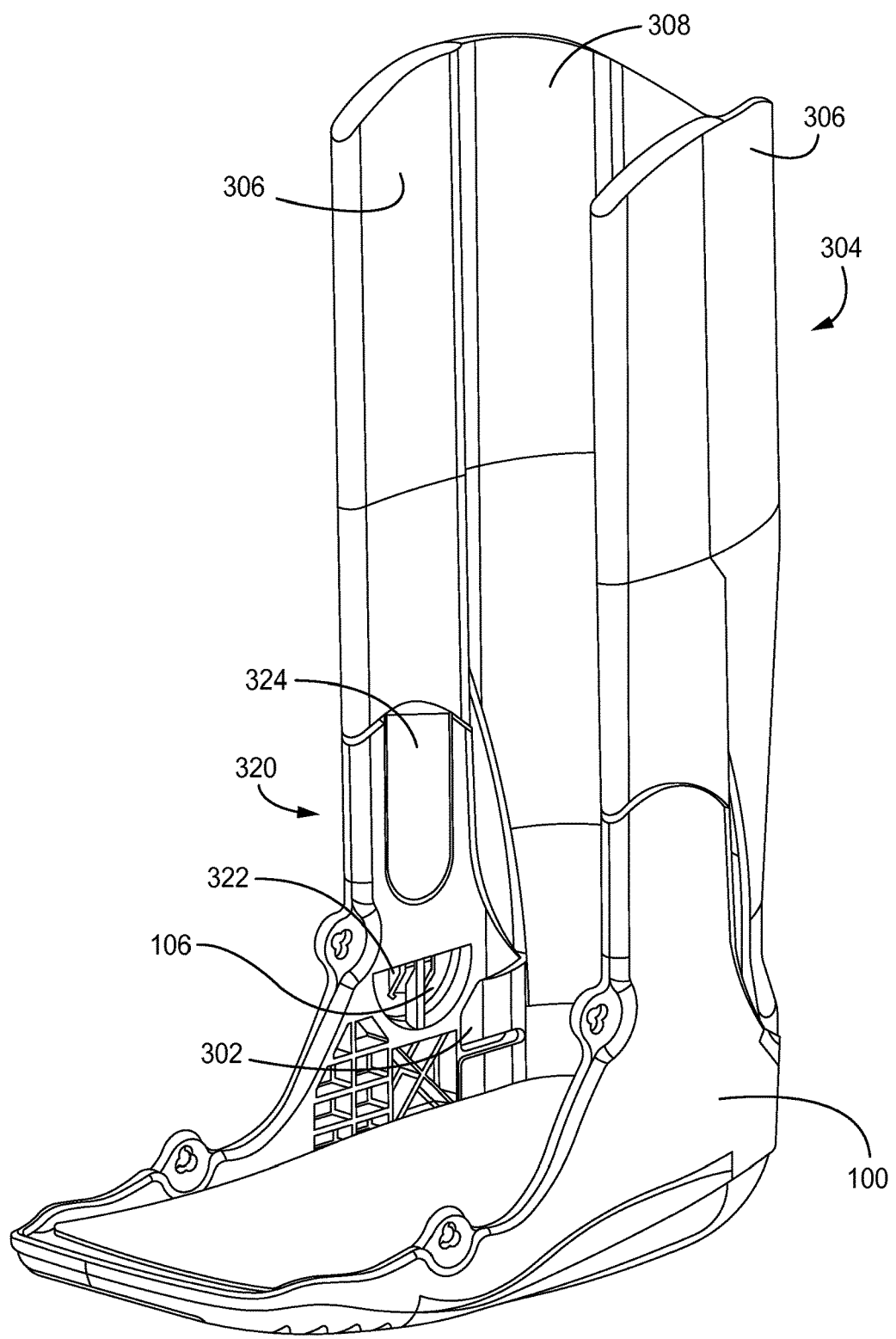
FIG. 5 is a perspective view of the base of FIG. 1 engaged with a clamshell structure in accordance with aspects of the present invention.

FIG. 5 shows a perspective view of another example embodiment where a clamshell structure 304 is mated with the base 100. FIG. 6 shows a perspective view the clamshell structure 304 exploded from the base 100. The clamshell structure 304 may include side portions 306 that service a similar function to the struts of the other example embodiments discussed above. The clamshell structure 304 may include a middle portion 308, thus providing a single continuous piece covering both the sides and the back of the leg. As shown in FIGS. 5 and 6 the clamshell structure 304 may include the equivalent features as the struts shown in FIGS.

3 and 4 for mating with the base 100. For example, the clamshell structure 304 may similarly include a male engagement portion 320, an alignment rib 324, a biasing member 322. In addition, the clamshell structure 204 may include additional engagement mechanisms 302 extending from the middle portion 308. The engagement mechanisms 302 may bias outwardly, i.e., in a direction toward the side portions 306. The engagement mechanisms 302 may be shaped to fit within the receiving elements 108 of the base 100.

When inserting the clamshell structure 304 into the base 100, the same steps as discussed above are performed with respect to mating the male engagement portion 320 with the engagement receiving portion 106. With respect to the engagement mechanism 302, the mechanism may be flexed inwardly (i.e., in a direction away from the side portions 306) by force to overcome the outward biasing force. Once the engagement mechanisms are 302 aligned with the receiving elements 108, the force can be removed, thereby allowing the engagement mechanisms 302 to bias back outwardly into the receiving elements 108. This provides a permanent engagement between the engagement mechanisms 302 and the receiving elements 108. Thus, as used herein, permanent means that the elements may be mated by the manufacturer/assembler such that the mated parts cannot be readily removed by the end user. For example, an end user would not be able to remove the mated parts absent the application of extreme force or tool assistance. As shown in FIG. 6, the clamshell structure 304 may include a second engagement portion, second alignment rib, and second bias member so that the clamshell 304 can engage with the base opposing sides of the base.

FIG. 7 is a side view of another example embodiment having non-continuous clamshell structure engaged with a base. FIG. 8 shows an exploded view of the non-continuous clamshell structure of FIG. 7. As shown in FIGS. 7 and 8, the non-continuous clamshell structure may include two separate side struts 404 opposing each other and a separate middle section 406, each being engagable with the base 100. The separate middle section 406 may include an engagement mechanism 402 similar to the middle portion discussed above with respect to the clamshell structure shown in FIG. 6. Similarly, the side struts 404 may each include a male engagement portion 420 similar to the male engagement portion discussed above with respect to the struts shown in FIG. 4 and the side portions shown in FIG. 6. The middle section 406 and the side struts 404 may engage with the base 100 in the same manner as the struts and clamshell structure discussed above. Additionally, a heel cushion 408 may be attached in a similar manner, allowing for a variety of configurations.

Figure 9:
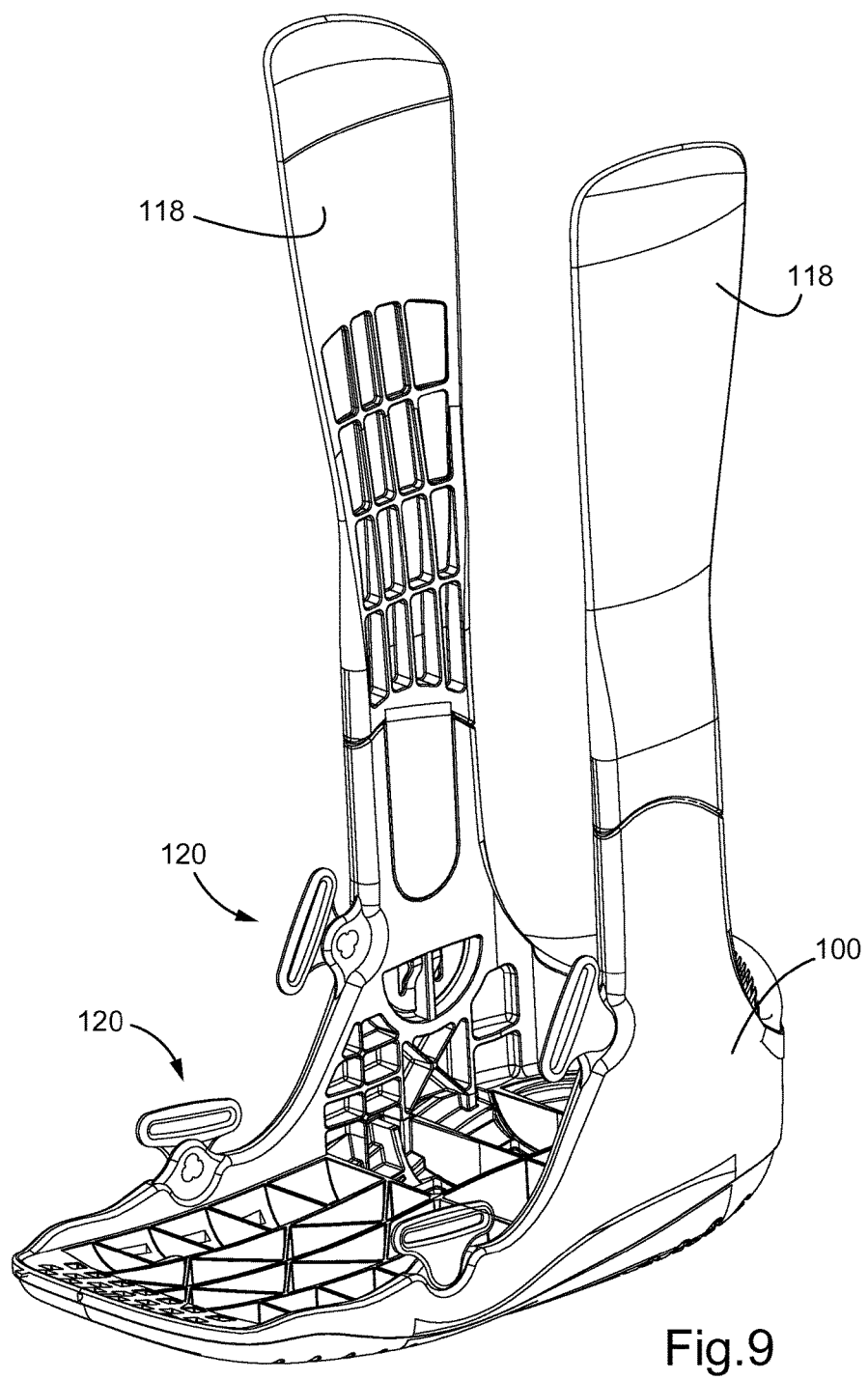
FIG. 9 is a perspective view of the base of FIG. 1 engaged with struts and strap anchors.
Figure 10:
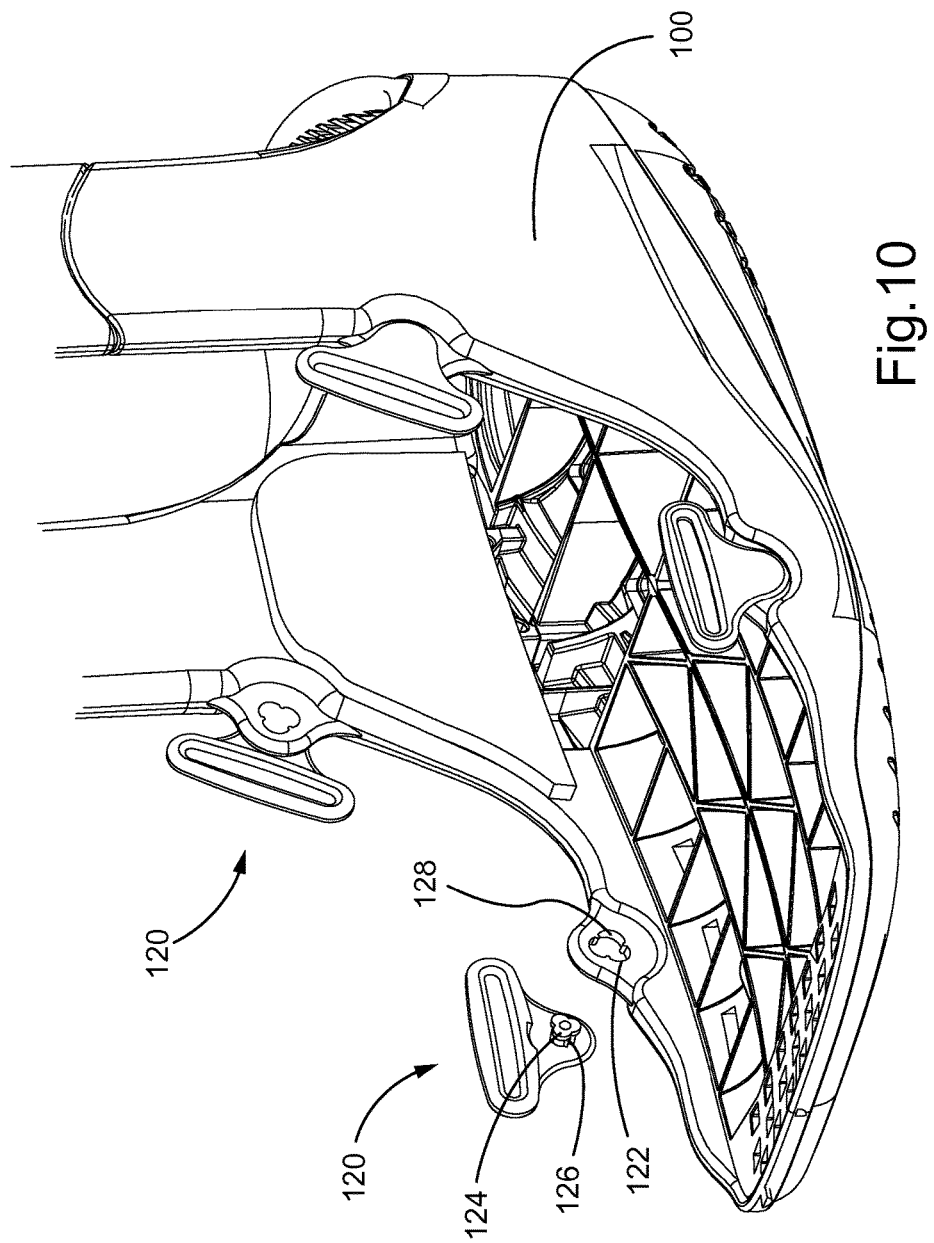
FIG. 10 is a partially exploded perspective view of the base of FIG. 1 with struts and strap anchors.

FIG. 9 is a perspective view of a base 100 coupled with struts 118 of FIG. 3 with strap anchors 120 (also known in the art as a chafe). FIG. 10 shows a close up view of the engagement of the strap anchors 120 with the base 100. The base 100 may include a receiving feature 122 shaped to receive a projection feature 124 extending from the strap anchor 120. As best seen in FIG. 10, one example geometry of the receiving feature 122 may be in the shape of a clover. The projection feature 124 may similarly have a clover shape. The projection feature 124 may include a plurality of one-way ribs 126. The one-way ribs 126 may have a ramp shape terminating into a flat wall such that when the projection feature 124 is pushed through the receiving feature 122, and then is rotated (either clockwise or counter-clockwise depending on the layout of the ribs 126), the ramp structure may allow projecting feature 124 to pass through the receiving feature 122, but prevent removal.

Figure 11:
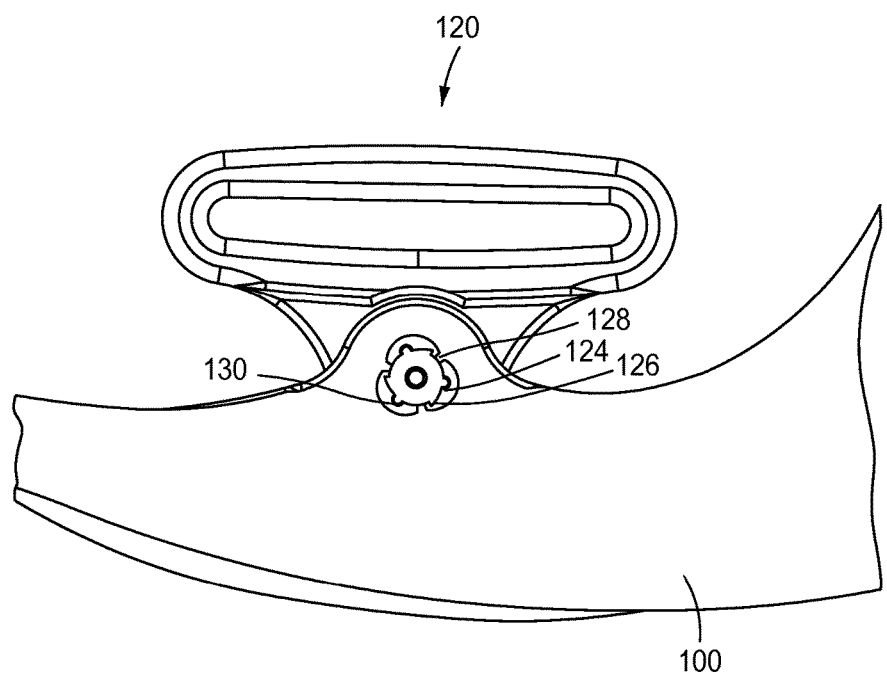
FIG. 11 is a close up side view of the base of FIG. 1 with an engaged strap anchor.

FIG. 11 shows a close up of a strap anchor 120 mated with the base 100. As shown in FIG. 11 the projection feature 124 may be inserted into a lateral position. As the anchor 120 is rotated, a ramp 126 rotates in a counterclockwise manner over a mating rib 128 on the base 100, allowing rotation back and forth only between the ramp 126 and a stop rib 130 on the projection feature 124.

Figure 12:
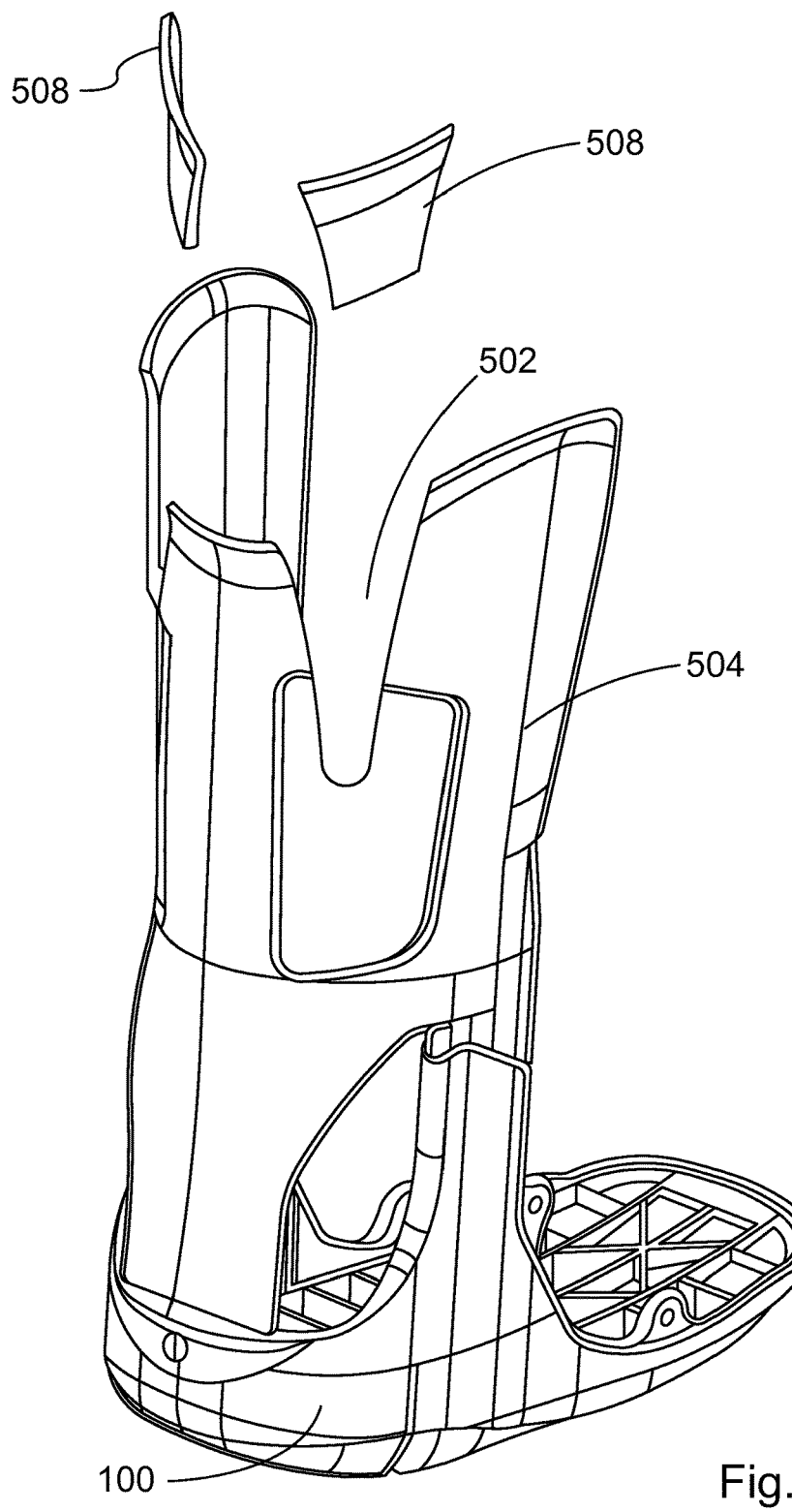
FIG. 12 is a partially exploded perspective view of the base of FIG. 1 engaged with a clamshell structure with exploded spacers.
Figure 13:
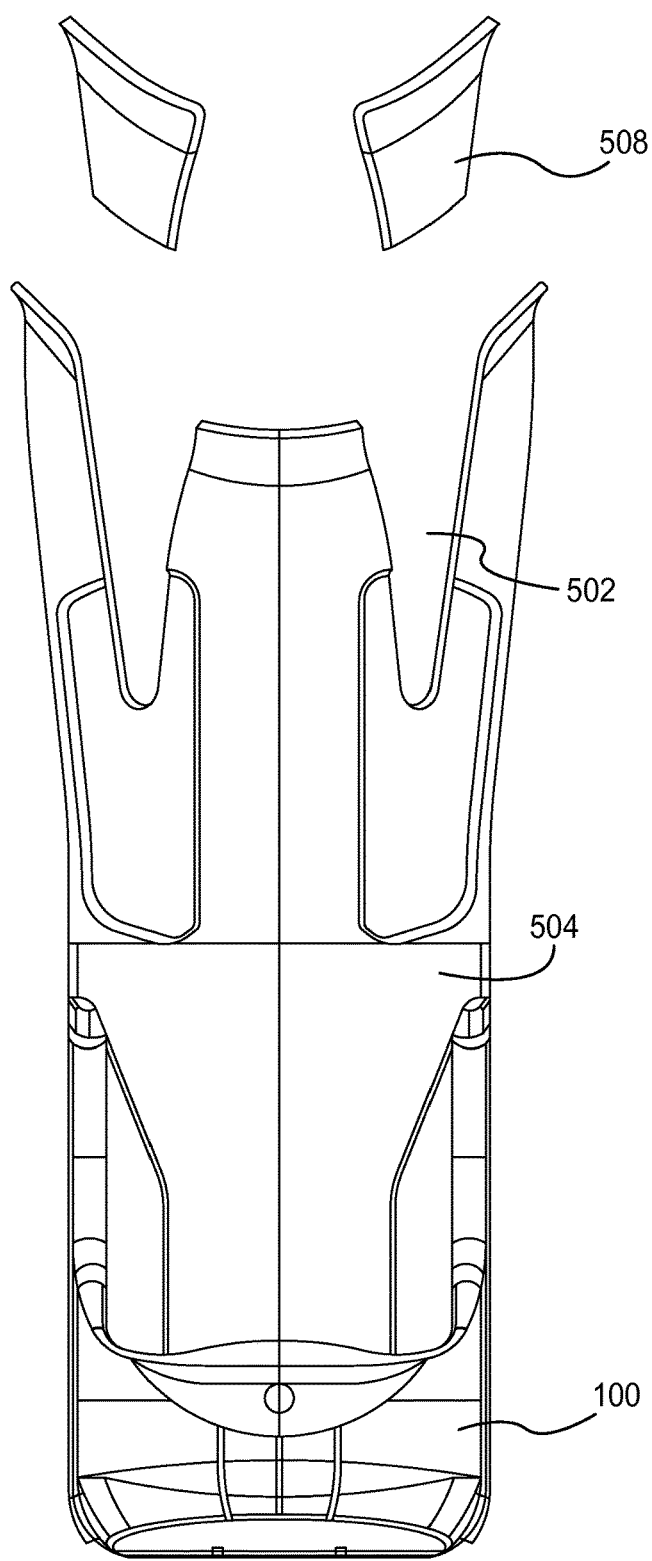
FIG. 13 is a partially exploded rear view of the base of FIG. 1 engaged with a clamshell structure with exploded spacers.
Figure 14:
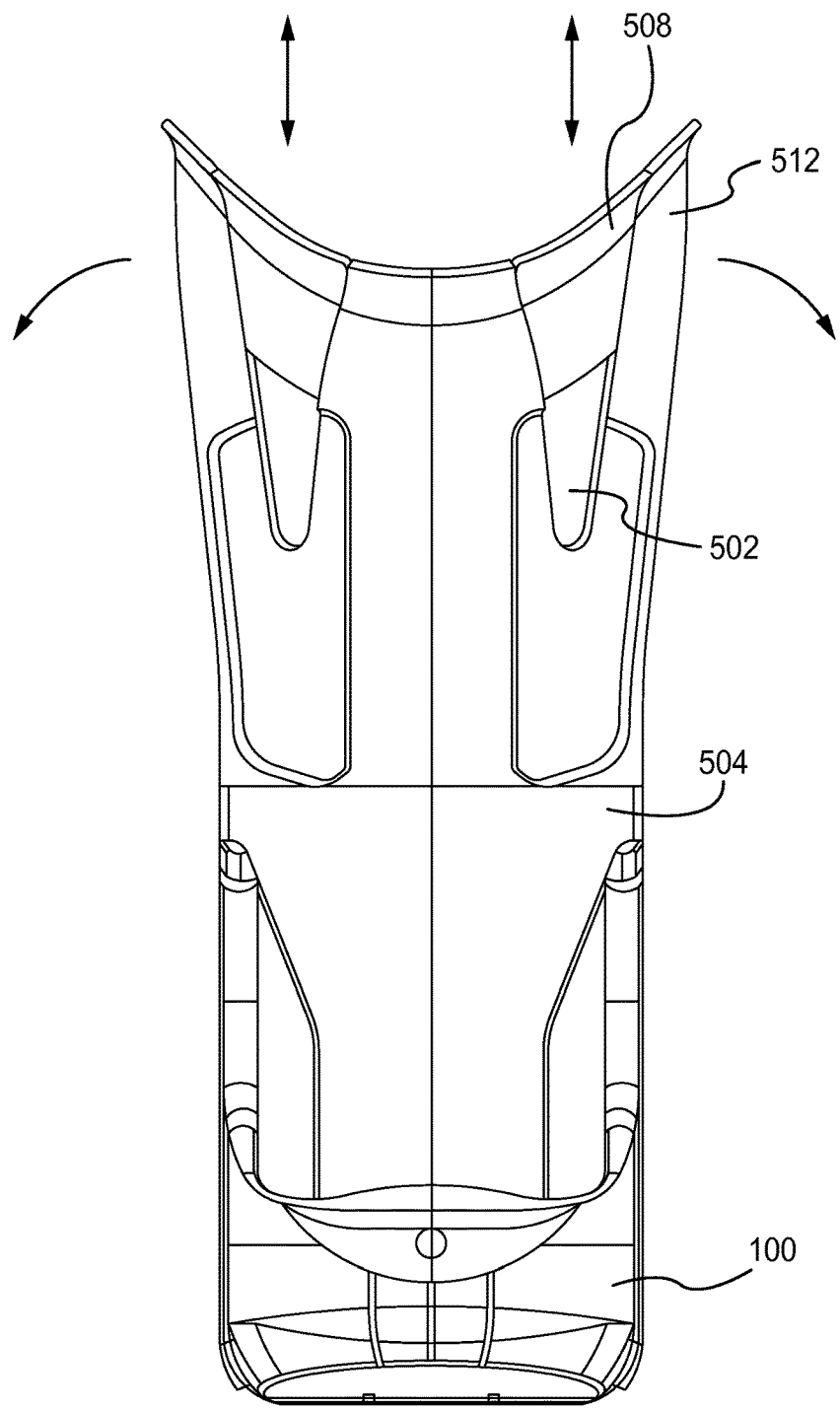
FIG. 14 is a rear view of the base of FIG. 1 engaged with a clamshell and spacers.

FIG. 12 is an exploded perspective view of another example embodiment of walking boot having a clamshell structure 500 for accommodating different calf sizing mated with a base 100. FIG. 13 is a rear view of the walking boot of FIG. 12 without spacers. FIG. 14 is a rear view of the walking boot of FIG. 12 without spacers. As shown in FIGS. 12-14, a plurality of vertical cuts 502 may be located in the clamshell structure 504. The cuts 502 may be positioned on a plurality of sides, with the opening of the cut larger at its uppermost location. A spacer 508 may be mated within each of the cuts 502. The spacer 508 may be removably engaged at different vertical locations of adjacent vertical cuts in the clamshell 504. The engagement serves to increase or decrease the gap of the vertical cut 502 which may provide more or less interior volume for the patient. Positive engagement of the spacers 508 to either end of the vertical cut may be achieved by any number of methods known to those skilled in the art, including but not limited to grooves, snaps, posts, pins, etc. As shown in FIG. 14 spacers 508 may be able to move in an attached or detached manner vertically along the vertical cut 502 allowing a vertical section 512 of the clamshell to rotate or otherwise deflect away from an initial position to provide more clearance inside the boot for patient anatomy. The spacers may be tethered or otherwise flexibly connected to facilitate ease of installation and adjustment.

Figure 15:
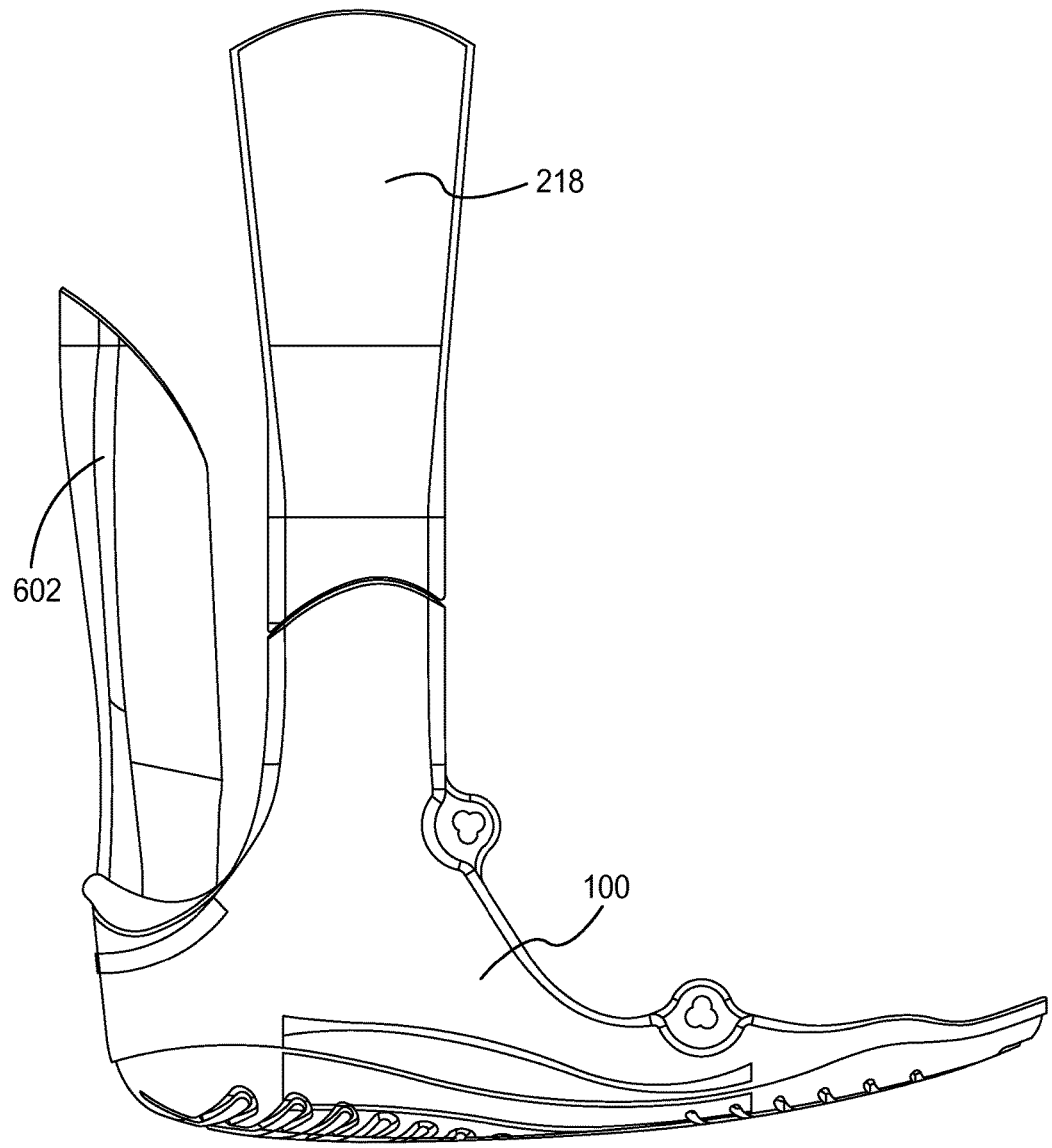
FIG. 15 is a side view of the base of FIG. 1 engaged with struts and a kick plate.
Figure 16:
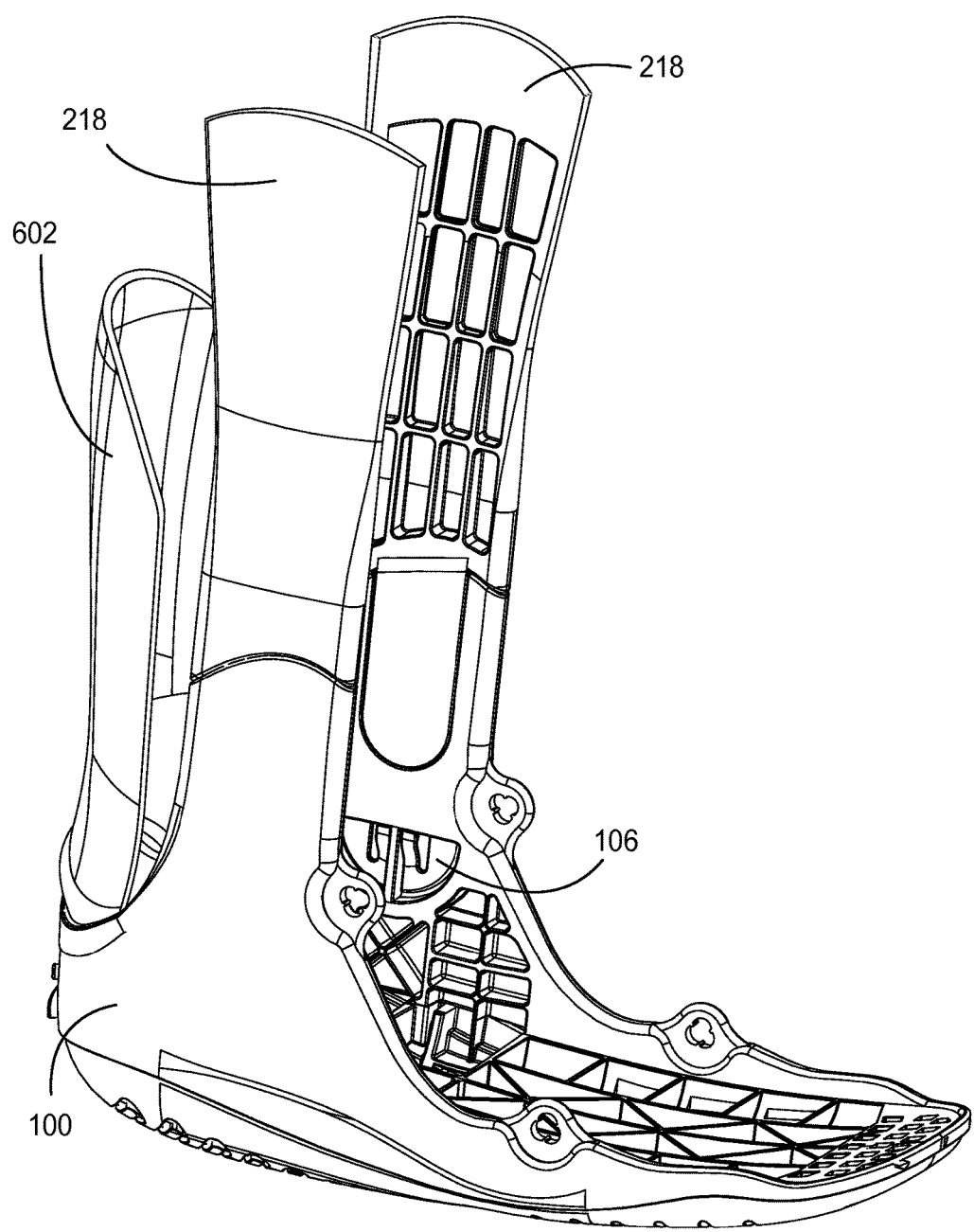
FIG. 16 is a perspective view of the base of FIG. 1 engaged with struts and a kick plate.

FIG. 15 shows a side view of another example aspect of a walking boot with a kick plate 602 engaged with the base 100. FIG. 16 shows a perspective view of the walking boot FIG. 15. The kick plate 602 may be a vertically disposed semi-rigid part intended to protect patient anatomy in the heel and calf region when assembled to a walker base or foundation part 100 as shown. As shown in FIG. 15, the kick plate may be mated with the base similar to the middle section 406 shown in FIG. 7.

The claims are not intended to be limited to the various aspects of this disclosure, but are to be accorded the full scope consistent with the language of the claims. It is noted that specific illustrative embodiments of the invention have been shown in the drawings and described in detail hereinabove. It is to be understood that various changes and modifications may be made without departing from the spirit and scope of the invention. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for."

What is claimed is:

1. An orthopedic walking boot, comprising:
a base configured to receive a user's foot having an outer sole, a foot bed configured to support a plantar portion of a user's foot, left and right uprights extending away from the foot bed, the left and right uprights including a capture cavity; and
a lower leg support member comprising first and second struts adapted to lock into respective left and right uprights at the capture cavity, and a middle portion posteriorly, circumferentially connecting the first and second struts to form a single continuous piece, the middle portion extending from a top of the first and second struts to the base, and further comprises a connector on a bottom edge that engages with the base to lock the lower leg support member to the base at a position posterior to the first and second struts, the connector comprising a pair of resiliently outwardly biased members that release to occupy respective openings in the base;
whereby an engagement of the first and second struts and the connector provides a three position anchor for the connection of the lower leg support member and the base.

2. The orthopedic walking boot of claim 1, wherein the lower leg support is an assembly including a circumferential spacer.

* * * * *